US010933198B2

(12) United States Patent
Holmqvist et al.

(10) Patent No.: US 10,933,198 B2
(45) Date of Patent: Mar. 2, 2021

(54) CAP ASSEMBLY AND A MEDICAMENT DELIVERY DEVICE COMPRISING THE CAP ASSEMBLY

(71) Applicant: Carebay Europe Ltd., Sliema (MT)

(72) Inventors: Anders Holmqvist, Värmdo (SE); Erik Miliander, Bromma (SE)

(73) Assignee: SHL MEDICAL AG, Zug (CH)

( * ) Notice: Subject to any disclaimer, the term of this patent is extended or adjusted under 35 U.S.C. 154(b) by 239 days.

(21) Appl. No.: 16/317,313

(22) PCT Filed: Jun. 27, 2017

(86) PCT No.: PCT/EP2017/065848
§ 371 (c)(1),
(2) Date: Jan. 11, 2019

(87) PCT Pub. No.: WO2018/010950
PCT Pub. Date: Jan. 18, 2018

(65) Prior Publication Data
US 2019/0247589 A1    Aug. 15, 2019

(30) Foreign Application Priority Data
Jul. 11, 2016  (EP) ..................... 16178876

(51) Int. Cl.
*A61M 5/32*      (2006.01)
*A61M 5/20*      (2006.01)

(52) U.S. Cl.
CPC ........ *A61M 5/3204* (2013.01); *A61M 5/3213* (2013.01); *A61M 5/20* (2013.01); *A61M 5/3202* (2013.01); *A61M 2205/192* (2013.01)

(58) Field of Classification Search
CPC .............. A61M 2205/192; A61M 5/20; A61M 5/3204; A61M 5/3213; A61M 5/3202; A61M 2005/3107; A61M 2005/3109; A61M 2005/311; A61M 5/3243
See application file for complete search history.

(56) References Cited

U.S. PATENT DOCUMENTS

2010/0286619 A1* 11/2010 Abry ................... A61M 5/2033
604/192

* cited by examiner

*Primary Examiner* — Bhisma Mehta
*Assistant Examiner* — Daniel Moore
(74) *Attorney, Agent, or Firm* — McDonnell Boehnen Hulbert & Berghoff LLP

(57) ABSTRACT

The disclosure relates to a cap assembly according to the present invention. The cap assembly comprises a medicament delivery device comprising a body having a proximal and a distal end. Further, the cap assembly comprises a graspable cap removably attached to the proximal end of the body. Further, the cap assembly comprises a graspable sleeve element having a proximal and a distal part, the sleeve element is arranged to at least partially enclose the body. The sleeve element is arranged to be non-removably attached to the body, but able to rotate relative to the body. The sleeve element is arranged to interact with the cap such that the cap is displaced proximally in relation to the body when the sleeve element is rotated relative to the body.

19 Claims, 6 Drawing Sheets

CAP ASSEMBLY AND A MEDICAMENT DELIVERY DEVICE COMPRISING THE CAP ASSEMBLY

CROSS REFERENCE TO RELATED APPLICATIONS

The present application is a U.S. National Phase Application pursuant to 35 U.S.C. § 371 of International Application No. PCT/EP2017/065848 filed Jun. 27, 2017, which claims priority to European Patent Application No. 16178876.5 filed Jul. 11, 2016. The entire disclosure contents of these applications are hereby incorporated by reference into the present application.

TECHNICAL FIELD

The present disclosure relates to the field of self-medication. In particular, the present disclosure relates to a cap assembly.

BACKGROUND ART

In the field of medicament delivery devices, there are a number of devices which have been developed for self-administration of medicaments. Many of these devices are provided with medicament containers, to which delivery members such as injection needles, inhalation mouth pieces etc. are attachable or integrated with.

The medicament delivery devices are generally equipped with a cap in order to protect either a needle or a docketing site arranged to receive a needle or an inhalation mouth piece etc. The cap is keeping the mouth piece, the docketing site or the needle of the medicament delivery device sterile, and also, when applicable, is protecting users from needle sticks when the medicament delivery device is not in use.

Typically, the action required to remove the cap from the medicament delivery device entails to pull the cap in a longitudinal direction away from the medicament delivery device. However, some patients may have difficulties to remove the cap from the medicament delivery device due to, for example, poor flexibility in their joints or due to weakness etc. In order to simplify the removal of the cap for those users, designs have been made where a rotation of the cap in relation to the medicament delivery device moves the cap in a longitudinal direction away from the medicament delivery device. A pulling force in a longitudinal direction away from the medicament delivery device usually still has to be performed on the cap in order to completely remove the cap from the medicament delivery device, but the required pulling force will not be as large.

However, medicament delivery devices where a cap is rotated in relation to the needle may be problematic. Due to the rotation of the cap in order to remove the cap, the needle might get damaged. There is a risk that the needle is bent or that the needle might break as the cap rotates around the needle. This may affect the function of the device. In addition, coring might occur. Coring is when the tip of the needle cuts out a piece of the material surrounding the needle when rotating the needle in relation to the surrounding material. This piece of material may then form a plug in the tip of the needle, disturbing further use of the medicament delivery device.

EP1755706 describes an injection device with a housing and a housing closure member with camming surfaces, wherein the camming surfaces communicate with each other so that rotation of the housing closure member about a longitudinal axis causes the housing closure member to move axially away from the housing. The invention according to this document involves a rotation of the cap relative to a needle.

There is a need for a cap assembly for a medicament delivery device for which the cap can be securely removed. There is also a need for a cap assembly which is designed to simplify the removal of the cap for users with poor flexibility in their joints. There is also a need for a robust cap assembly which minimizes the risk of interfering with the needle as the cap is removed and at the same time is simple to manufacture.

SUMMARY

In view of the above mentioned problems with the current cap assemblies, there is a need to improve the current cap assemblies. Thus, it is an object of the present invention to provide an improved or at least an alternative cap assembly which meets one or more of the above-mentioned challenges of conventional cap assemblies.

The above objects are achieved with a cap assembly according to the present disclosure. The cap assembly comprises a medicament delivery device comprising a body, elongated along a longitudinal axis, and having a proximal and a distal end. Further, the cap assembly comprises a cap, graspable by the hand of a user, and removably attached to the proximal end of the body, wherein the cap is rotationally locked in relation to the body. Further, the cap assembly comprises a sleeve element having a proximal and a distal part, the sleeve element being graspable by the hand of a user, the sleeve element is arranged to at least partially enclose the body. The sleeve element is arranged to be non-removably attached to the body, but able to rotate relative to the body. The sleeve element is arranged to interact with the cap such that the cap is displaced proximally in relation to the body when the sleeve element is rotated relative to the body.

By using a sleeve element to displace the cap proximally, an alternative construction of a cap assembly is achieved. A person with poor flexibility in their joints or weakness etc. will find it easier to rotate the sleeve element in relation to the cap and to the body and thereby displacing the cap proximally in relation to the body than exerting a pulling force on the cap in a proximal direction in order to displace the cap. When using the cap assembly, the sleeve and the cap are held by the user and the sleeve element is rotated around or in relation to the body, and in relation to the cap. However, the sleeve element will not come loose from the body, but will remain attached to the body after removal of the cap. With this construction, the user will find it easy to remove the cap from the body. If the sleeve element completely encloses the body, the user may not see that the cap is rotationally locked in relation to the body. The cap assembly according to the presented teaching is a robust device which is simple to manufacture.

According to one aspect of the disclosure at least a proximal part of the sleeve element and at least a distal part of the cap form a connecting interface.

According to one aspect of the disclosure, the sleeve element is arranged to interact with the cap via the connecting interface. Further, the cap is displaced proximally in relation to the body via the connecting interface when the sleeve element is rotated from a first position to a second position in relation to the body.

The rotation of the sleeve element around the body causes a proximal displacement of the cap in relation to the body.

By defining a first and a second position of the sleeve element in relation to the body, a user of the device will find it easy to use. This construction is a robust and simple construction which is simple to produce.

According to one aspect of the disclosure a locking mechanism is arranged on the inner circumferential surface of the sleeve element and the outer circumferential surface of the body. The locking mechanism is arranged to lock the sleeve element in relation to the body.

The locking mechanism simplifies the use of the cap assembly. Once the locking mechanism is activated, the sleeve element will be locked in relation to the body such that when the user is using the medicament delivery device, there are no moving parts which will interfere with the use of the medicament delivery device. The sleeve element and the body will form a unit and the user can remove the cap and inject the drug without any interference of any additional moving parts.

Further, according to one aspect of the disclosure, the locking mechanism is activated when the sleeve element is in the second position in relation to the body.

By activating the locking mechanism when the sleeve element is in the second position, the user could get an indication that the required rotational movement for displacing the cap has been performed and hence this construction simplifies the use of the cap assembly.

According to one aspect of the present disclosure, the sleeve element comprises a first inspection window which is arranged to be aligned with at least one corresponding second inspection window of the body when the sleeve element is in the second position in relation to the body.

By having an inspection window in the sleeve element and a corresponding inspection window in the body, the medicament can be inspected before use. During the inspection, the amount and quality of the medicament may be controlled. In addition, the user will be able to verify that a certain amount of medicament has been distributed after use of the medicament delivery device. This increases the safety for the user of cap assembly. In addition, the medicament is protected from unwanted UV-rays when the assembly is not in use, i.e. before the sleeve element has been rotated to the second position in relation to the body.

According to one aspect of the present disclosure the cap is rotationally locked in relation to the body by means of at least one first guide arranged on the interior surface of the cap, and at least one first guide follower arranged on the exterior surface of the proximal end of the body of the medicament By fixating the cap in a rotational direction in relation to the body, it can be assured that the cap is displaced proximally when the sleeve element rotates in relation to the body The guide and the guide follower lock the cap in a rotational direction in relation to the body, hence, when the sleeve element rotates in relation to the body, the sleeve element also rotates in relation to the cap. However, the guide and the guide follower allow a longitudinal movement of the cap in relation to the body.

A guide and a guide follower is a reliable construction for locking two parts in a rotational direction in relation to each other. The guide and guide follower are also easy to manufacture and form a robust construction.

According to one aspect of the disclosure, the connecting interface is configured such that the cap is displaced proximally in relation to the body when the sleeve element and the cap are rotated in relation to each other.

By constructing or designing the connection interface in a manner such that the cap is displaced proximally in relation to the body and in relation to the sleeve element when the sleeve element is rotated in relation to the body and to the cap, a simple and robust construction is achieved. With this construction, no additional parts have to be added in order to achieve a proximal movement of the cap as the sleeve element is rotated around the body.

According to one aspect of the disclosure at least part of the connecting interface is shaped as a cam surface that is slanted in relation to a plane perpendicular to a longitudinal axis of the cap assembly to exert a proximally directed force on the cap when the sleeve element is rotated in relation to the cap.

By configuring the connecting interface such that the cap may be displaced proximally in relation to the body when the sleeve element is rotated in relation to the body and also in relation to the cap, for example by making part of the connecting interface a cam surface, a simple and robust construction which accomplishes the proximal displacement of the cap as the sleeve element is rotated in relation to the body, is achieved.

According to one aspect of the disclosure the sleeve element is longitudinally locked in relation to the body by engagement between at least one second guide arranged on the interior circumferential surface of the sleeve element, and at least one second guide follower arranged on the exterior circumferential surface of the body.

A second guide and a second guide follower form a robust and simple solution which locks the sleeve element in relation to the body in a longitudinal direction. Thereby, due to the configuration of the connecting interface the cap is displaced in a proximal direction when the sleeve element is rotated in relation to the body and in relation to the cap. This is a simple and robust construction which is user friendly.

According to one aspect of the disclosure at least part of the inner circumferential surface of the sleeve element and a corresponding part of the outer circumferential surface of the body comprise third guide structures. The third guide structures are arranged such that the sleeve element is displaced proximally in relation to the body, whereby the cap is displaced proximally, when the sleeve element and the body are rotated in relation to each other.

An alternative way of displacing the cap in a proximal direction in relation to the body is to equip the sleeve element and the body with the third guide structures, e.g. threads. This is an alternative robust and simple construction which achieves a movement of the cap in a proximal direction as the sleeve element and the body are rotated in relation to each other. The threads will cause a proximal movement of the sleeve element as the sleeve element is rotated around the body. This proximal movement of the sleeve element will further cause the cap to be moved proximally away from the body due to the connecting interface between the cap and the sleeve element.

BRIEF DESCRIPTION OF THE DRAWINGS

In the following description of embodiments of the proposed technique, reference will be made to the accompanying drawings of which.

DETAILED DESCRIPTION

In the present application, when the term "distal" is used, this refers to the direction pointing away from the medicament delivery site. When the term "distal part/end" is used, this refers to the part/end of the cap assembly, or the parts/ends of the members thereof, which under use of the cap assembly is/are located farthest away from the medicament delivery site. Correspondingly, when the term "proximal" is used, this refers to the direction pointing to the medicament delivery site. When the term "proximal part/end" is used, this refers to the part/end of the cap assembly, or the parts/ends of the members thereof, which under use of the cap assembly is/are located closest to the medicament delivery site.

Further, the term "longitudinal", with or without "axis", refers to a direction or an axis through a medicament delivery device comprising the cap assembly or components thereof in the direction of the longest extension of the delivery device. A rotational motion is herein always defined as a rotation around the longitudinal axis.

The term "lateral", with or without "axis", refers to a direction or an axis through the medicament delivery device or components thereof in the direction of the broadest extension of the device.

In a similar manner, the terms "radial" or "transversal", with or without "axis", refers to a direction or an axis through the medicament delivery device or components thereof in a direction generally perpendicular to the longitudinal direction, e.g. "radially outward" would refer to a direction pointing away from the longitudinal axis.

Also, if nothing else is stated, in the following description wherein the mechanical structure of the cap assembly and the mechanical interconnection of its components are described, the cap assembly is in an initial non-activated, closed or non-operated state.

The medicament delivery assembly illustrated in the figures is an injector, but could in practice be any kind of delivery device having a cap that has to be removed prior to administration of its contents such as an inhalation device etc.

The guide and guide follower illustrated in the figures are of a certain construction, but could be any kind of guide and guide follower known in the art. According to one example, the guide and the guide follower are formed out of a recess and a protruding element constructed to fit in the recess. According to another example, the guide and the guide follower are formed out of two protruding bodies forming a gap between them and a protruding body such as a ridge fitting into the gap. The guide and the guide follower are interchangeable.

Figure 1:
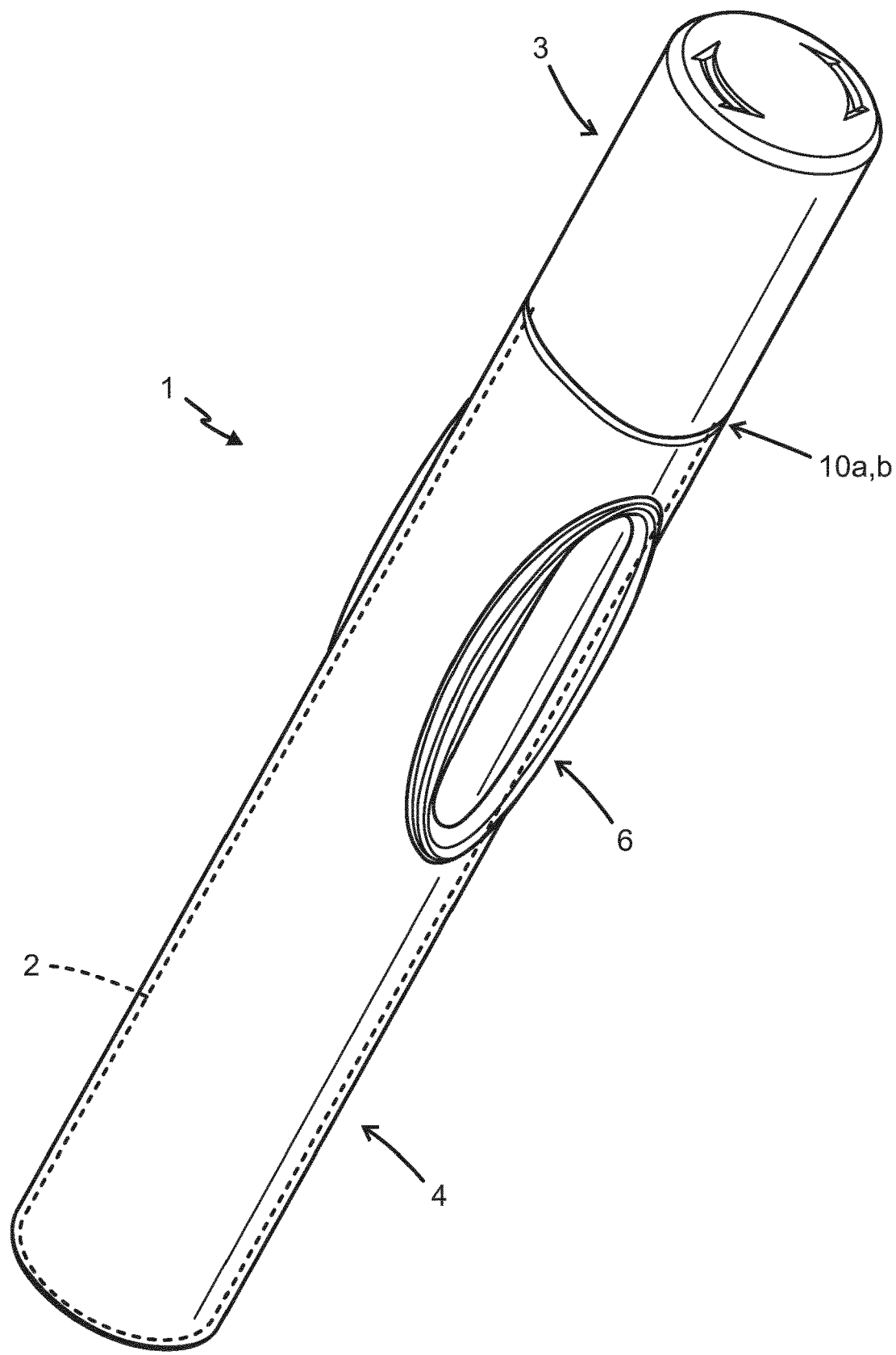
FIG. 1 is a perspective view of the cap assembly according to one aspect of the disclosure.

FIG. 1 illustrates a cap assembly 1 comprising a cap 3 and a sleeve element 4 enclosing at least a part of a body 2 of a medicament delivery device 2. The cap 3 is removably attached to the body 2.

The cap 3 has preferably a tubular shape with a distal open end. The cap 3 is arranged to at least partially enclose the proximal end of the body 2 when the cap assembly 1 is in a closed state.

The sleeve element 4 has a preferably tubular shape with a proximal part, e.g. a proximal end and a distal part, e.g. a distal end. The proximal part is essentially parallel to a plane which is perpendicular to the longitudinal axis of the assembly. The sleeve element 4 is arranged to at least partially enclose the body 2. In FIG. 1, the sleeve element 4 encloses the whole body 2. At least a proximal part of the sleeve element 4 is arranged to engage with at least a distal part of the cap 3 when the cap assembly 1 is in a closed state. The proximal part of the sleeve element 4 and the distal part of the cap 3 which are arranged to engage with each other form a connecting interface 10a, 10b.

According to one exemplary aspect of the present disclosure, the sleeve element 4 comprises two openings, one proximal opening at the proximal part and one distal opening (not illustrated) at a distal part.

The body 2 is a longitudinally elongated, preferably tubular body which comprises a least a part of a medicament delivery device, such as an auto-injector, a pen injector, an inhalation or a spray device, or a syringe, including a medicament container and a docketing site arranged to receive a needle or a mouth piece etc, attached at the proximal end of the body 2. Alternatively, a fixed needle or mouth piece is integrated with the docketing site of the body 2. The body 2 is at least partially enclosed by the cap 3 at the proximal end of the body 2 when the cap assembly 1 is in a closed state. The sleeve element 4 is arranged to be able to rotate relative to the body 2 and in relation to the cap 3. This can, according to one embodiment, be achieved by means of at least a second guide and a second guide follower arranged on the exterior circumferential surface of the body 2 and on the interior circumferential surface of the sleeve element 4. The second guide and second guide follower allow a rotational movement of the sleeve element 4 in relation to the body 2 and the cap 3 but prevents a longitudinal movement of the sleeve element 4 in relation to the body 2 and the cap 3.

The cap 3 and the sleeve element 4 are connected via a connecting interface 10a, 10b. The cap 3 is displaced in a longitudinal direction away from the body 2 when the sleeve element 4 and the body 2 are rotated in relation to each other. When a user wants to remove the cap 3 from the medicament delivery device 1 he preferably grips the sleeve element 4 with one hand and the cap 3 with the other hand. The user performs a rotational movement of the sleeve element 4 in relation to the body 2 and in relation to the cap 3. When a rotation of the sleeve element 4 is performed in relation to the body 2, the cap 3 is displaced in a proximal direction in relation to the body 2.

When the rotation has been performed and the cap 3 has been displaced a certain distance x in a proximal direction in relation to the body 2, the cap 3 can then be removed completely from the body 2 by applying a small force on the cap 3 in a proximal direction away from the body 2.

The sleeve element 4 comprises a first inspection window 6 and the body 2 comprises a second inspection window 7. These windows 6, 7 will be described further in relation to FIG. 2.

Figure 2:
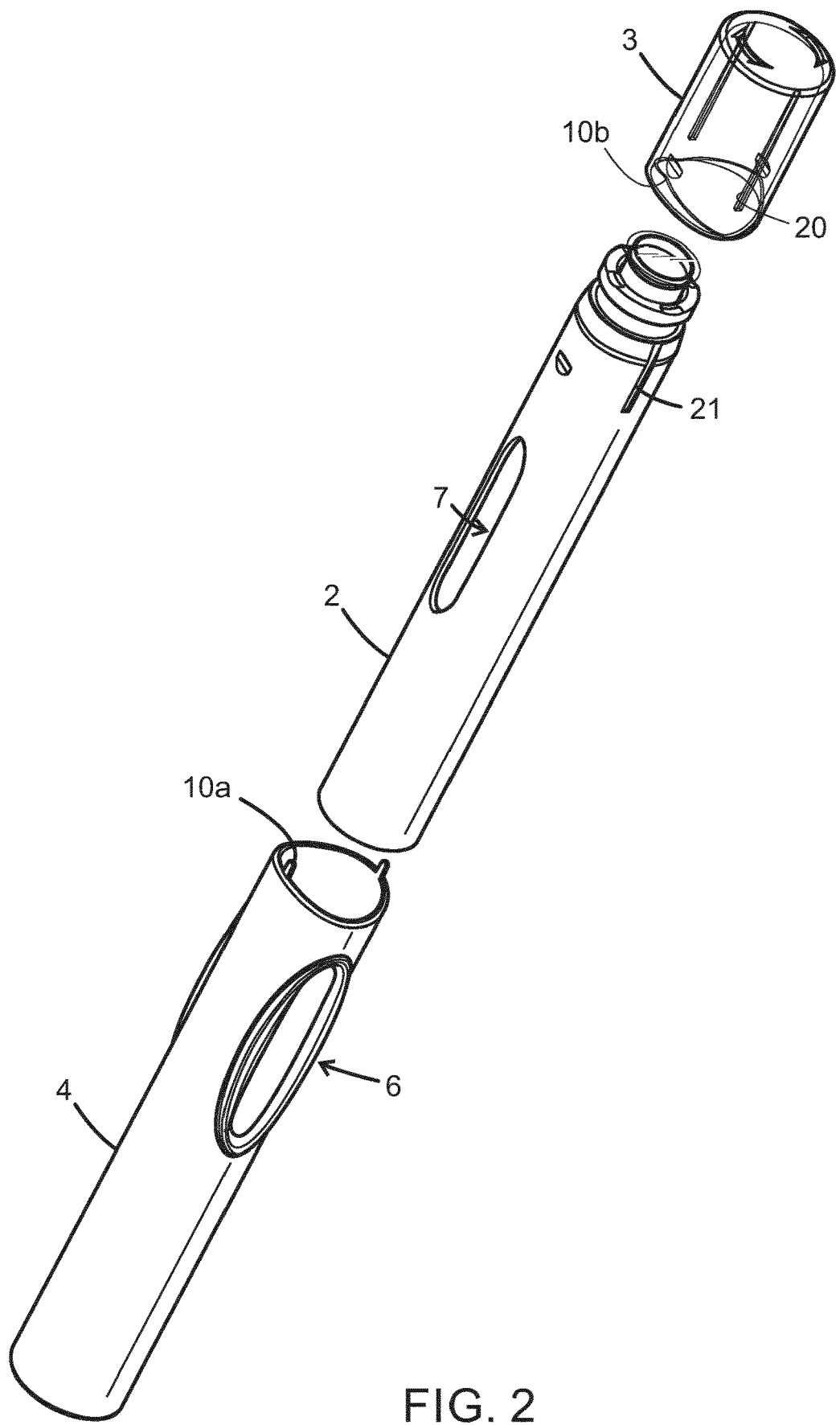
FIG. 2 is an exploded perspective view of the cap assembly according to one aspect of the disclosure.

FIG. 2 illustrates an exploded view of the cap assembly 1. The sleeve element 4 at least partially encloses the body 2, when assembled. The sleeve element 4 comprises a first inspection window 6 through which the medicament can be inspected visually before, during and after delivery of said medicament. The body 2 comprise a second inspection window 7. The second inspection window 7 of the body 2 may have any shape and size as long as it overlaps with the first inspection window 6 of the sleeve element 4 when the sleeve element 4 and the body 2 are in a certain rotational position in relation to each other, for example, when the sleeve element 4 is in a second position in relation to the body 2. In addition, the first inspection window 6 and the second inspection window 7 are arranged to not overlap when the cap assembly 1 is in a closed state.

According to one aspect of the disclosure, the medicament can be inspected before delivery of the medicament, when the sleeve element 4 has been moved to a second position in relation to the body 2 for which position the inspection windows 6, 7 overlap. The amount of medicament and the visual impression of the medicament in the medicament delivery device 1 may be investigated before use. During delivery of the medicament, it can be assured that the medicament is delivered by inspecting the medicament through the inspection windows 6, 7. After delivery of the medicament it can be visually confirmed via the inspection windows 6, 7, that a certain volume, for example the whole amount, of the medicament, has been delivered. When the cap assembly 1 is in a closed state, the first inspection window 6 and the second inspection window 7 do not overlap, and hence, the medicament is protected from UV-light.

The cap 3 comprises a first guide 20 arranged on at least a part of the interior surface of the cap 3. A first guide follower 21 is arranged on the proximal end of the body 2 being in contact with the cap 3 when the assembly 1 is in a closed state. The first guide 20 and the first guide follower 21 rotationally lock the cap 3 and the body 2 in relation to each other. Thereby, when the sleeve element 4 is rotated in relation to the body 2, the sleeve element 4 is also rotated in relation to the cap 3 while the cap 3 is rotationally fixed in relation to the body 2.

Figure 3A:
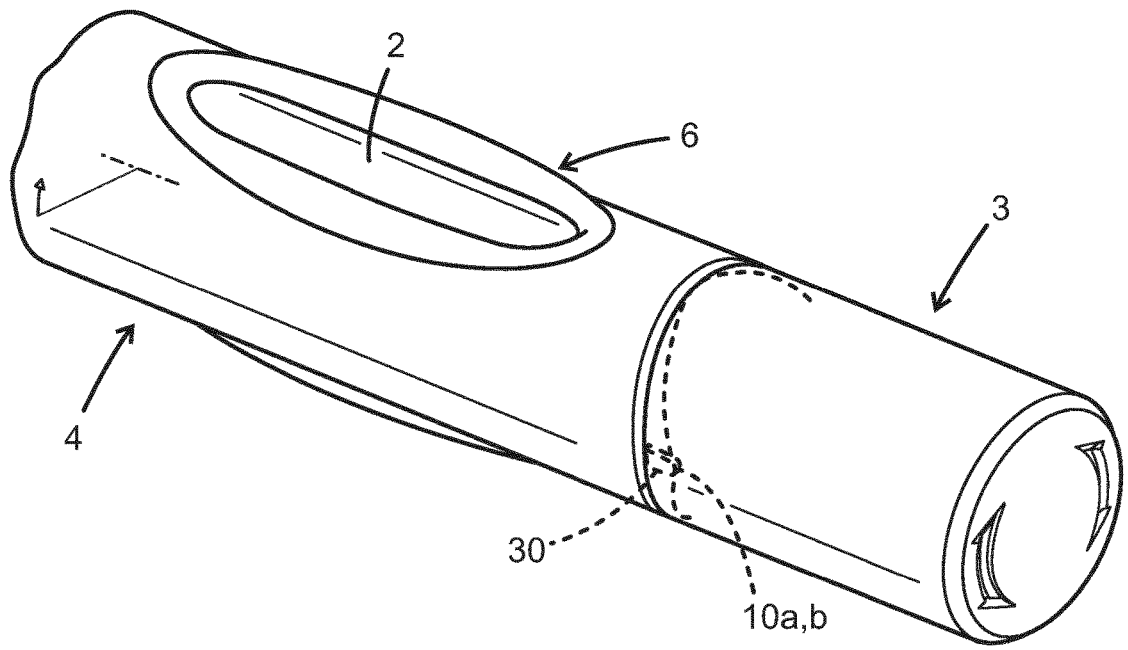
FIG. 3a is a perspective view of the cap assembly in a closed state according to one aspect of the disclosure.
Figure 3B:
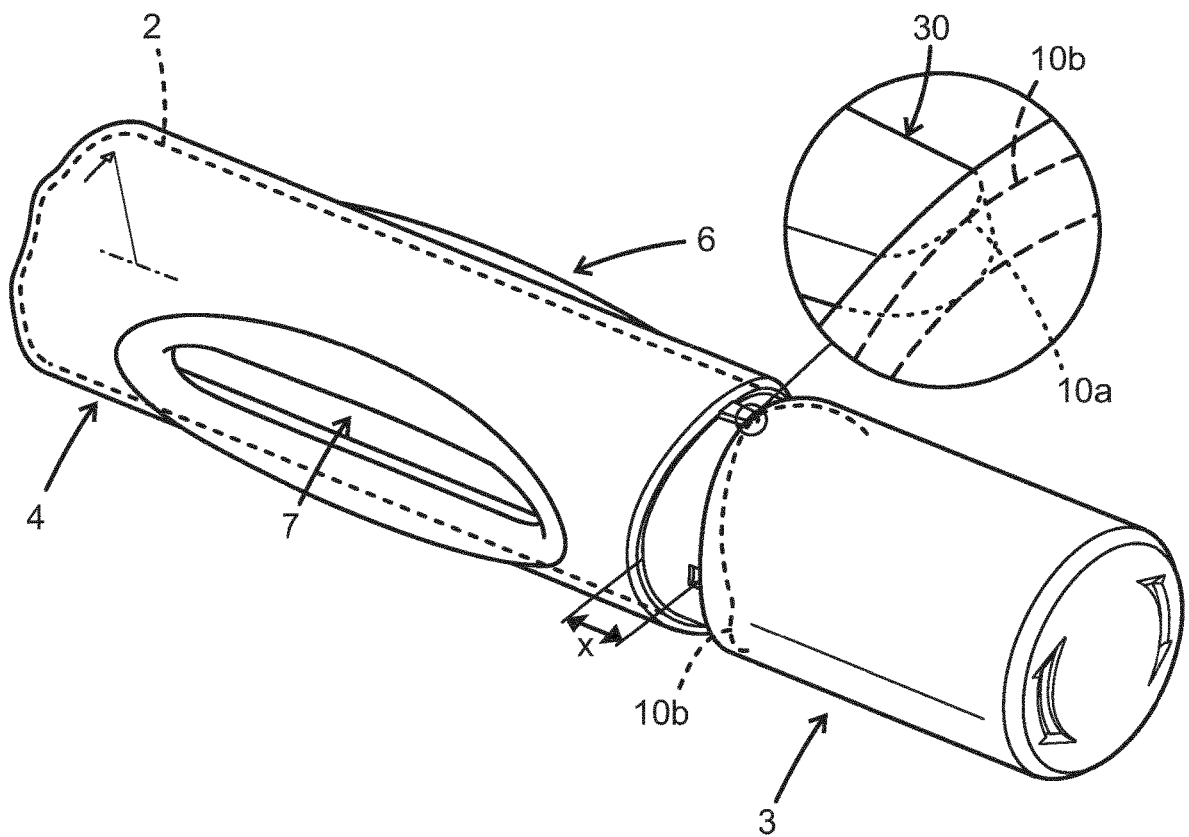
FIG. 3b is a perspective view of the cap assembly in an open state according to one aspect of the disclosure.

FIGS. 3a and 3b illustrate the cap assembly 1 in further detail. FIG. 3a discloses the cap 3 and the proximal part of the sleeve element 4 and part of the body 2 when the cap assembly 1 is in in a closed state or in a first position. The connecting interface 10a, 10b is formed out of at least a part of a circumferential surface forming the opening at the proximal part of the sleeve element 4 and at least a part of a circumferential surface forming the distal opening of the cap 3. At least part of the circumferential surface of the sleeve element 4 and at least a part of a circumferential surface of the cap 3 are in contact with each other forming a connecting interface 10a, 10b. The first inspection window 6 of the sleeve element 4 is not aligned and does not overlap with the second inspection window 7 and hence, the drug is protected from UV-light.

The connecting interface 10a, 10b is configured or designed such that the cap 3 is displaced proximally in relation to the body 2 when the sleeve element 4 is rotated in relation to the body 2 and the cap 3. According to one embodiment of the present disclosure, the sleeve element 4 is rotated from a first position illustrated in FIG. 3a to a second position illustrated in FIG. 3b. During the rotation of the sleeve element 4 in relation to the body 2 and the cap 3 at least part of a circumferential proximal end surface 10a of the proximal part of the sleeve element 4 and at least a part of a circumferential distal surface 10b of the distal part of the the cap 3 are in contact forming a connecting interface 10a, 10b. Due to the design or construction of the connecting interface 10a, 10b, the rotational movement of the sleeve element 4 pushes the cap 3 away from the body 2 in a proximal direction.

Once the cap 3 has been displaced in a proximal direction by rotating the sleeve element 4 in relation to the body 2 and the cap 3, that is, when the sleeve element 4 has been rotated to a second position in relation to the body 2, the cap assembly 1 is in an open state. FIG. 3b illustrates the placement of the parts of the cap assembly 1 in an open state. As can be seen, the cap 3 has been displaced a certain distance x in a proximal direction away from the body 2 via the connecting interface 10a, 10b due to the rotation of the sleeve element 4 in relation to the body 2 from a first position (FIG. 3a) to a second position (FIG. 3b). The distance x is dependent on the construction or design of the connecting interface 10a, 10b.

According to one embodiment of the present disclosure, the connecting interface 10a, 10b is formed out of at least a part of a circumferential end surface of the distal part of the cap 3 and at least one protruding element 30 of the proximal part of the sleeve element 4. The protruding element 30 could alternatively be placed on the distal part of the cap 3 (not illustrated). When the cap assembly 1 is in a closed state, the protruding element 20 on the proximal part of the sleeve element 4 is connected to the lower part of a cam surface of the cap 3, see FIG. 3a. The cam surface of the cap 3 is slanted in relation to a direction of rotation end of the cap 3, i.e. in relation to an axial direction of the cap assembly 1. As the sleeve element 4 is rotated in relation to the body 2 and the cap 3, the protruding element 30, placed on the proximal part of the sleeve element 4 will slide along the slanted cam surface of at least a part of the distal circumferential surface of cap 3 until it reaches the higher part of the slanted cam surface, see FIG. 3b. Due to this rotational movement, the cap 3 will be pushed in a proximal direction away from the body 2. Hence, when the sleeve element 4 is rotated from a first position, which is illustrated in FIG. 3a, to a second position, which is illustrated in FIG. 3b, the cap 3 is pushed a distance x away from the body 2.

In the second position, the first inspection window 6 and the second inspection window 7 are aligned, and hence, the drug can be inspected through the aligned first and second inspection windows 6, 7.

Figure 3C:
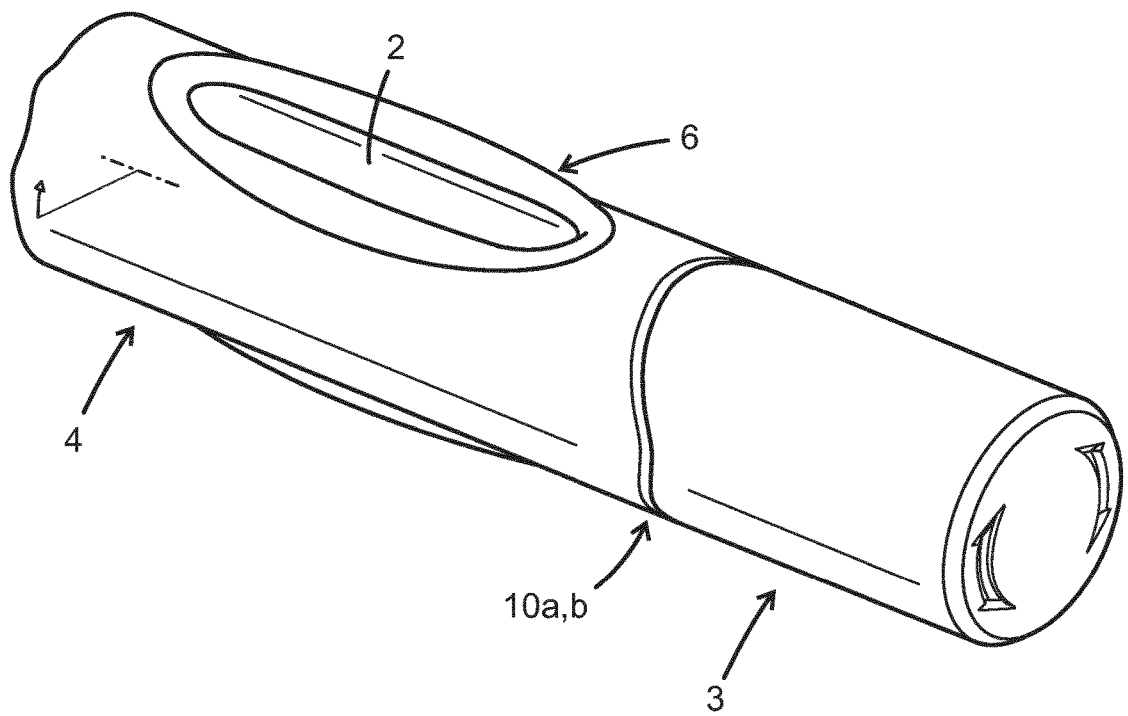
FIG. 3c is a perspective view of the cap assembly in a closed state according to one aspect of the disclosure.
Figure 3D:
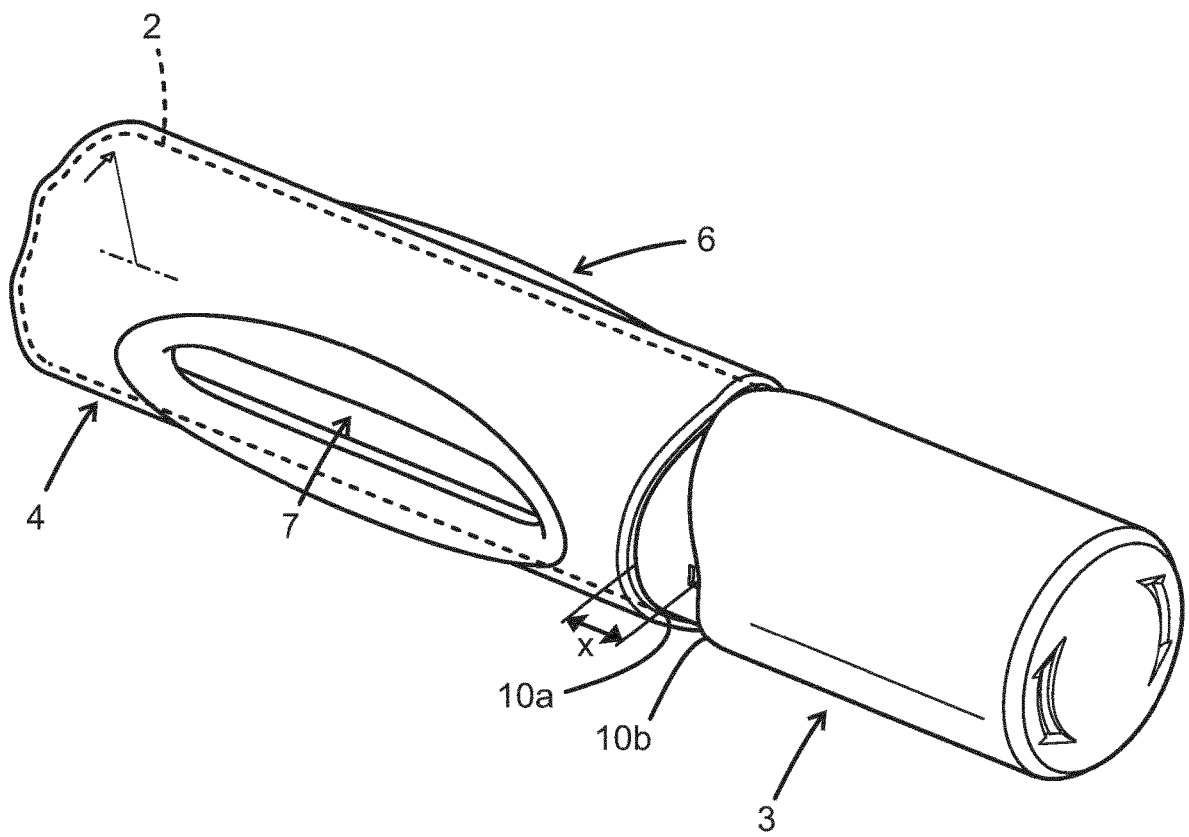
FIG. 3d is a perspective view of the cap assembly in an open state according to one aspect of the disclosure.

FIGS. 3c and 3d illustrate the cap assembly 1 in an open and a closed state according to another embodiment of the disclosure. In this embodiment, at least a proximal part of the sleeve element 4 as well as the distal part of the cap 3 forming the connecting interface 10a, 10b, are designed in, for example, a wave form, or at least partially slanting relative to a plane perpendicular to the longitudinal axis. This design achieves the same effect as the protruding element 30 and a cam surface illustrated in FIG. 3a, 3b when the sleeve element 4 is rotated in relation to the body 2.

There are also other designs of the connecting interface 10a, 10b which can achieve the desired effect and these designs are also covered by this disclosure.

The connecting interface 10a, 10b may, according to one exemplary embodiment, be enclosed either by the sleeve element 4 or the cap 3 or both. Hence the connecting interface 10a, 10b might not be visible to a user of the cap assembly 1.

When the sleeve element 4 has been rotated to a second position in relation to the body 2, the cap 3 has been displaced a distance x in a proximal direction in relation to the body 2 via the connecting interface 10a, 10b. The cap 3 is however, according to one embodiment, still attached to the body 2 after the rotation of the sleeve element 4 from a first position to a second position, but only a small pulling force in a proximal direction is required from the user in order to remove the cap 3 completely from the body 2. According to another aspect of the present disclosure, the cap 3 is removed completely when the sleeve element 4 has been rotated to a second position in relation to the body 2 and the cap 3.

Figure 4A:
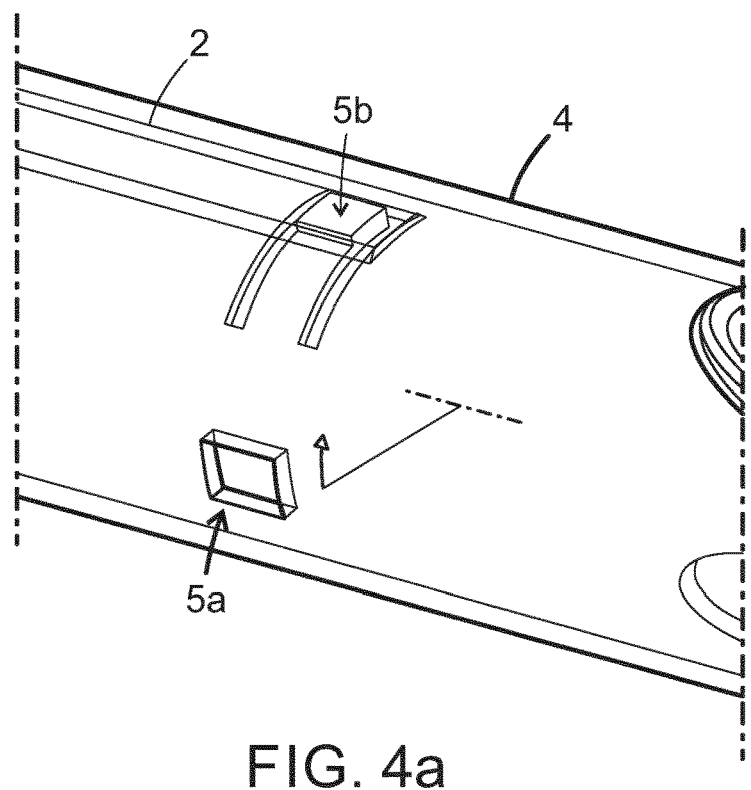
FIG. 4a is a perspective view of part of the cap assembly and a non-activated locking mechanism according to one aspect of the present disclosure.
Figure 4B:
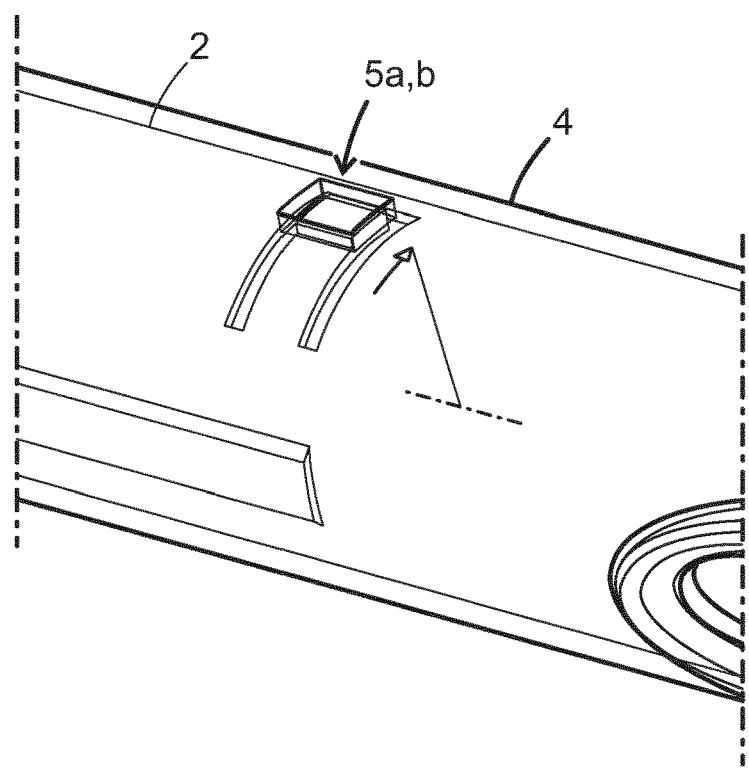
FIG. 4b is a perspective view of part of the cap assembly and an activated locking mechanism according to one aspect of the present disclosure.

FIG. 4a and FIG. 4b illustrate a locking mechanism 5a, 5b arranged on the inner circumferential surface of the sleeve element 4 and the outer circumferential surface of the body 2. FIG. 4a illustrates the locking mechanism 5a, 5b in a non-activated state. When the locking mechanism 5a, 5b is not activated, the sleeve element 4 is not restricted by the locking mechanism 5a, 5b and can hence move in relation to the body 2.

FIG. 4b illustrates the locking mechanism 5a, 5b in an active state. The locking mechanism 5a, 5b is activated when the sleeve element 3 is in the second position in relation to the body 2 and the cap 3. The locking mechanism 5a, 5b is arranged to lock the sleeve element 4 in relation to the body 2, both in a longitudinal and a rotational direction. The locking mechanism 5a, 5b is a position locking mechanism, well known to a person skilled in the art. The locking mechanism 5a, 5b could for example be a hinge lock. In the second position when the locking mechanism 5a, 5b has been activated, the cap 3 has been displaced in a proximal direction a distance x in relation to the body 2. In addition, the first inspection window 6 of the sleeve element 4 is aligned with a corresponding second inspection window 7 of the body 2. Hereby, the medicament can be inspected before, during and after delivery, but, the medicament is protected from UV-rays at all other times before the removal of the cap 3 has been initiated.

Figure 5A:
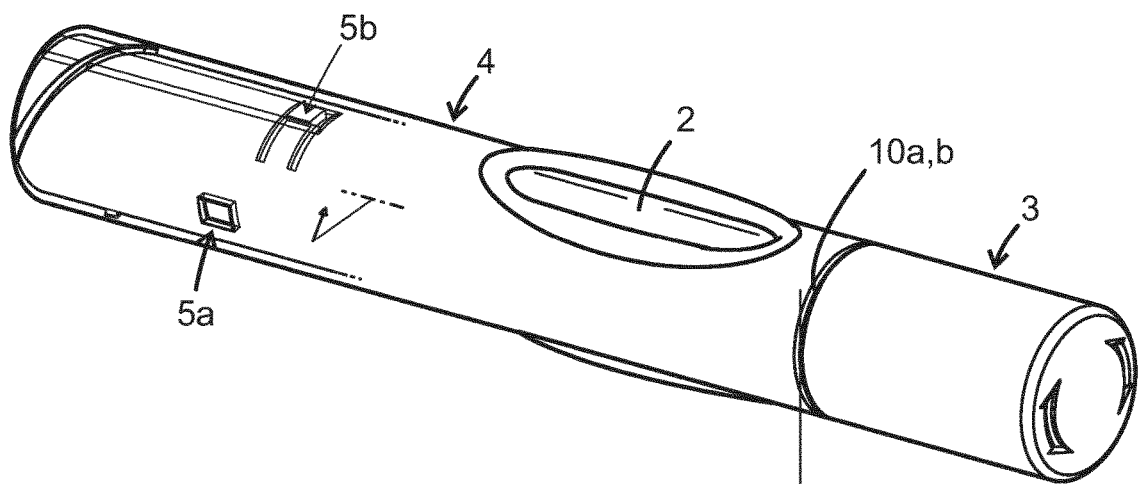
FIG. 5a is a perspective view of the cap assembly in a closed state according to one aspect of the disclosure.
Figure 5B:
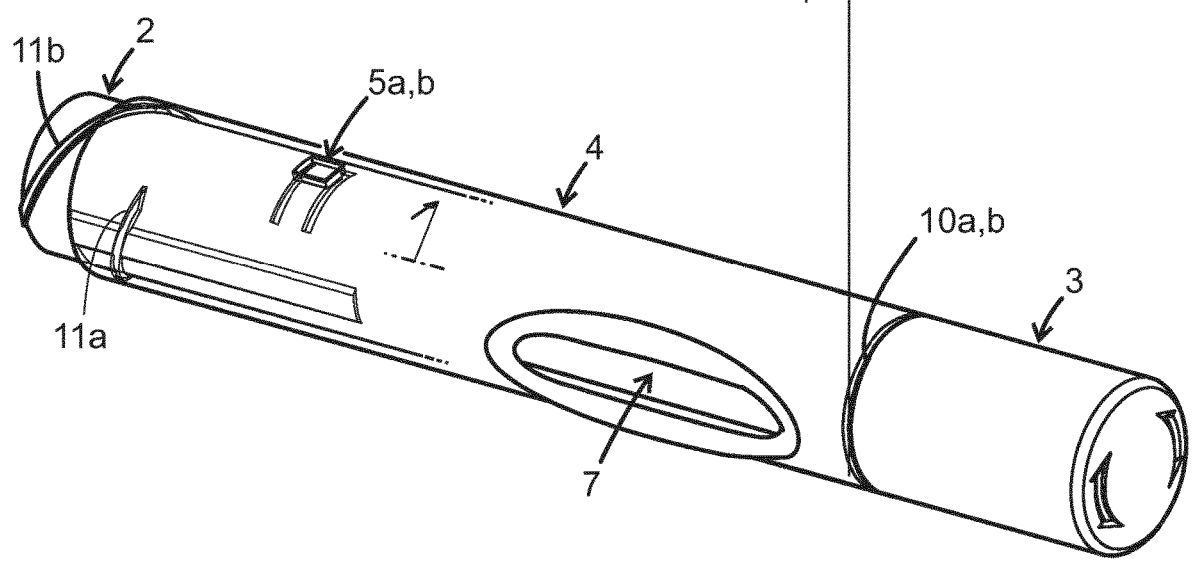
FIG. 5b is a perspective view of the cap assembly in an open state according to one aspect of the disclosure.

FIGS. 5a and 5b illustrate the cap assembly 1 in further detail. FIG. 5a illustrates the cap assembly 1 in a closed state or in a first position. According to this embodiment at least part of the inner circumferential surface of the sleeve element 4 and a corresponding part of the outer circumferential surface of the body 2 comprise third guide structures 11a, 11b. The third guide structures 11a, 11b are arranged such that the sleeve element 4 is displaced proximally in relation to the body 2 when the sleeve element 4 and the body 2 are rotated in relation to each other. The third guide structures 11a, 11b may comprise threads. FIG. 5b illustrates the cap assembly 1 in a second position, when the sleeve element 4 has been rotated to a second position. The rotation of the sleeve element 4 in relation to the body 2 causes a movement of the sleeve element 4 in a longitudinal direction in relation to the body 2. This movement of the sleeve element 4 pushes the cap 3 in a proximal direction, away from the body 2, via the connecting interface 10a, 10b. When the sleeve element has rotated to a second position in relation to the body 2 and in relation to the cap 3, this rotational and longitudinal movement of the sleeve causes the cap 3 to move a distance x in a longitudinal direction away from the body 2 as illustrated in FIG. 5b. The movement of the sleeve element in a longitudinal direction cause the cap 3 to move in a longitudinal direction via the connecting interface 10a, 10b. According to this embodiment, the third guide structures 11a, 11b may be configured so that when the sleeve element 4 is rotated from a first position to a second position in relation to the body 2 the sleeve element 4 has rotated part of a revolution, such as 90 to 120 degrees, around the body 2. According to this embodiment, the connecting interface 10a, 10b may be formed out of two flat surfaces, substantially parallel to a plane orthogonal to the longitudinal axis.

It is to be understood that the embodiments described above and shown in the drawings is to be regarded only as a non-limiting example of the present disclosure and that it may be modified in many ways within the scope of the patent claims.

The invention claimed is:

1. A cap assembly comprising:
   a body of a medicament delivery device, elongated along a longitudinal axis, and having a proximal and a distal end,
   a cap, graspable by the hand of a user, and removably attached to the proximal end of the body, wherein the cap is rotationally locked in relation to the body characterized in that the cap assembly further comprises:
   a sleeve element having a proximal and a distal part, the sleeve element being graspable by the hand of a user, the sleeve element is arranged to at least partially enclose the body, the sleeve element is arranged to be non-removably attached to the body, but able to rotate relative to the body, the sleeve element is arranged to interact with the cap such that the cap is displaced proximally in relation to the body when the sleeve element is rotated relative to the body,
   wherein the cap is rotationally locked in relation to the body by engagement of at least one first guide arranged on an interior surface of the cap with at least one first guide follower arranged on an exterior surface of the proximal end of the body.

2. A cap assembly according to claim 1 wherein at least a proximal part of the sleeve element and at least a distal part of the cap form a connecting interface.

3. A cap assembly according to claim 2, wherein at least part of the connecting interface is configured such that the cap is displaced proximally in relation to the body when the sleeve element and the cap are rotated in relation to each other.

4. A cap assembly according to claim 3, wherein at least part of the connecting interface is shaped as a cam surface that is slanted in relation to a plane perpendicular to a longitudinal axis of the cap assembly to exert a proximally directed force on the cap when the sleeve element is rotated in relation to the cap.

5. A cap assembly according to claim 3, wherein the sleeve element is longitudinally locked in relation to the body by engagement between: at least one second guide arranged on an interior circumferential surface of the sleeve element, and at least one second guide follower arranged on an exterior circumferential surface of the body.

6. A cap assembly according to claim 1 wherein the sleeve element is arranged to interact with the cap via the connecting interface and wherein the cap is displaced proximally in relation to the body via the connecting interface when the sleeve element is rotated from a first position to a second position in relation to the body.

7. A cap assembly according to claim 6, wherein the sleeve element comprises a first inspection window which is arranged to be aligned with at least one corresponding second inspection window of the body when the sleeve element is in the second position in relation to the body.

8. A cap assembly according to claim 1, wherein a first part of a lock is arranged on an inner circumferential surface of the sleeve element and a second part of the lock is arranged on an outer circumferential surface of the body, wherein the lock is arranged to lock the sleeve element in relation to the body.

9. A cap assembly according to claim 8, wherein the lock is activated when the sleeve element is in a second position in relation to the body.

10. A cap assembly according to claim 1, wherein at least part of an inner circumferential surface of the sleeve element and a corresponding part of an outer circumferential surface of the body comprise third guide structures arranged such that the sleeve element is displaced proximally in relation to the body, whereby the cap is displaced proximally, when the sleeve element and the body are rotated in relation to each other.

11. A cap assembly according to claim 10, wherein the third guide structures comprise threads.

12. A medicament delivery device comprising a cap assembly according to claim 1.

13. A cap assembly for a medicament delivery device comprising:
- a body of a medicament delivery device, elongated along a longitudinal axis, and having a proximal and a distal end,
- a cap, graspable by the hand of a user, and removably attached to the proximal end of the body, wherein the cap is rotationally locked in relation to the body, the cap assembly comprising:
- a sleeve element having a proximal and a distal part, the sleeve element being graspable by the hand of a user, the sleeve element is arranged to at least partially enclose the body, the sleeve element is arranged to be non-removably attached to the body, but able to rotate relative to the body, the sleeve element is arranged to interact with the cap such that the cap is displaced proximally in relation to the body when the sleeve element is rotated relative to the body, wherein at least a distal part of the cap forms a connecting interface with the sleeve element, wherein the cap is rotationally locked in relation to the body by engagement of at least one first guide arranged on an interior surface of the cap with at least one first guide follower arranged on an exterior surface of the proximal end of the body.

14. The cap assembly as claimed in claim 13, wherein the distal part of the cap and at least a proximal part of the sleeve element forms the connecting interface.

15. The cap assembly according to claim 13 wherein the sleeve element is arranged to interact with the cap via the connecting interface.

16. The cap assembly of claim 15 wherein the cap is displaced proximally in relation to the body via the connecting interface.

17. The cap assembly of claim 16, wherein the cap is displaced proximally in relation to the body via the connecting interface when the sleeve element is rotated from a first position to a second position in relation to the body.

18. The cap assembly according to claim 13, wherein a first part of a lock is arranged on an inner circumferential surface of the sleeve element.

19. The cap assembly of claim 18 wherein a second part of the lock is arranged on the sleeve element to lock the sleeve element in relation to the body.

* * * * *